US006458322B1

(12) United States Patent
Harris

(10) Patent No.: US 6,458,322 B1
(45) Date of Patent: Oct. 1, 2002

(54) METHOD FOR SIMPLIFIED SHIPPING OF CLINICAL SPECIMENS AND OPTIONAL DIRECT ANALYSIS

(75) Inventor: James W. Harris, Cocoa Beach, FL (US)

(73) Assignee: Bioavailability Systems, LLC, Cocoa Beach, FL (US)

( * ) Notice: Subject to any disclaimer, the term of this patent is extended or adjusted under 35 U.S.C. 154(b) by 0 days.

(21) Appl. No.: 09/658,111

(22) Filed: Sep. 8, 2000

(51) Int. Cl.[7] .................................................. A61L 2/00
(52) U.S. Cl. ............................... 422/28; 422/1; 435/29; 435/287.1; 435/288.1; 424/93.1
(58) Field of Search .................. 435/29, 287.1, 435/288.1; 422/1, 28; 424/93.1

(56) References Cited

U.S. PATENT DOCUMENTS

| | | | |
|---|---|---|---|
| 1,594,370 A | 8/1926 | Kubota | 206/438 |
| 3,163,160 A | 12/1964 | Cohen | 206/229 |
| 3,418,209 A * | 12/1968 | Ushakoff | 435/2 |
| 3,913,564 A | 10/1975 | Freshley | 600/572 |
| 3,915,806 A | 10/1975 | Horlach | 435/307.1 |
| 4,014,748 A | 3/1977 | Spinner et al. | 600/572 |
| 4,150,950 A * | 4/1979 | Takeguchi et al. | 435/252.1 |
| 4,196,167 A | 4/1980 | Olsen | 422/61 |
| 4,211,323 A * | 7/1980 | Olsen | 206/210 |
| 4,311,792 A | 1/1982 | Avery | 435/30 |
| 4,336,880 A | 6/1982 | Mehl | 206/524.8 |
| 4,340,670 A | 7/1982 | Mennen | 435/25 |
| 4,353,868 A | 10/1982 | Joslin et al. | 422/101 |
| 4,387,725 A | 6/1983 | Mull | 422/59 |
| 4,513,008 A * | 4/1985 | Revici et al. | |
| 4,557,902 A | 12/1985 | Mussmann | 422/59 |
| 4,604,360 A | 8/1986 | Hounsell | 435/287 |
| 4,732,850 A | 3/1988 | Brown et al. | 435/31 |
| 4,740,475 A | 4/1988 | Paul | 436/165 |
| 4,770,853 A | 9/1988 | Bernstein | 422/58 |
| 4,788,985 A | 12/1988 | Manning et al. | 128/759 |
| 4,813,432 A | 3/1989 | Saint-Amand | 128/749 |
| 4,978,504 A | 12/1990 | Nason | 422/61 |
| 5,078,968 A | 1/1992 | Nason | 422/58 |
| 5,138,034 A | 8/1992 | Uemura et al. | 530/413 |
| 5,238,649 A * | 8/1993 | Nason | 422/58 |
| 5,256,537 A * | 10/1993 | Phillips et al. | 435/7.1 |
| 5,266,266 A | 11/1993 | Nason | 422/58 |
| 5,313,959 A | 5/1994 | Monthony et al. | 128/759 |
| 5,362,654 A * | 11/1994 | Pouletty | 436/518 |
| 5,425,915 A | 6/1995 | Phillips et al. | 422/58 |
| 5,511,558 A | 4/1996 | Shepard et al. | 600/573 |
| 5,633,349 A * | 5/1997 | Reichl | 530/364 |
| 5,658,531 A | 8/1997 | Cope et al. | 422/58 |
| 5,710,041 A | 1/1998 | Moorman et al. | 435/287.6 |
| 5,726,062 A * | 3/1998 | Numa et al. | 436/86 |
| 5,786,227 A * | 7/1998 | Charlton | 436/177 |
| 5,786,228 A * | 7/1998 | Charlton | 436/177 |
| 5,827,675 A * | 10/1998 | Skiffington et al. | 435/8 |
| 5,859,374 A * | 1/1999 | Mink et al. | 73/863 |
| 5,869,003 A * | 2/1999 | Nason | 422/58 |
| 5,879,635 A * | 3/1999 | Nason | 422/102 |
| 5,996,799 A * | 12/1999 | Garreth et al. | |

FOREIGN PATENT DOCUMENTS

| GB | 1 542 411 | 8/1976 |
|---|---|---|

OTHER PUBLICATIONS

Amitava Dasgupta, et al.; *Effect of Heating Human Sera at a Temperature Necessary to Deactivate Human Immunodeficiency Virus on Measurement of Free Phenytoin, Free Valproic Acid, and Free Carbamazepine Concentrations*; Therapeutic Drug Monitoring, vol. 21, No. 4, pp. 421–425, 1999.

Specialty Laboratories, Test with Order Codes Beginning with Letter 1; p. 1–11.

Specialty Laboratories, Test with Order Codes Beginning with Letter 2; p. 2–7.

Specialty Laboratories, Test with Order Codes Beginning with Letter 3; p. 1–9.

J.D. Druce, et al.; *Susceptibility of HIV to inactivation by disinfectants and ultraviolet light*; Journal of Hospital Infection (1995) 30, pp. 167–180.*

Barbara Thompson McKinnon, et al., *Membrane filtration of pharm aceutical solutions*; Am J Hosp Phar., vol. 50, pp. 1921–1936, Sep. 1993.*

Lionel Resnick, et al; *Stability and Inactivation of HTLV–III/LAV Under Clinical and Laboratory Environments*; The Journal of the American Association, vol. 255, No. 14, pp. 1887–1891; Apr. 11, 1986.*

J. O'Grady, et al.; *Virus Removal Studies Using Nanofiltration Membranes*; Brown F. Lubiniecki AS: Viral Safety and Evaluation of Viral Clearance from Biopharmaceutical Products. Dev Biol Stand. Basel, Karger, 1996, vol. 88, pp. 319–326.*

Specialty Laboratories; Tests with Order Codes Beginning with Letter 4; p. 1–6.

Specialty Laboratories; Tests with Order Codes Beginning with Letter 5; p. 1–12.

Specialty Laboratories, Tests with Order Codes Beginning with Letter 6; p. 1.

Specialty Laboratories; Tests with Order Codes Beginning with Letter 7; p. 1–5.

Specialty Laboratories; Tests with Order Codes Beginning with Letter 8; p. 1–6.

Specialty Laboratories; Tests with Order Codes Beginning with Letter 9; p. 1–5.

(List continued on next page.)

Primary Examiner—Ralph Gitomer
Assistant Examiner—Mahreen Chaudhry
(74) Attorney, Agent, or Firm—Oblon, Spivak, McClelland, Maier & Neustadt, P.C.

(57) ABSTRACT

A method for shipping clinical specimens lawfully, safely, cheaply, and easily without regard to some or all of the laws, rules, and regulations regarding samples that may contain infectious and/or etiologic agents. Optional method of direct analysis of shipped samples.

20 Claims, No Drawings

OTHER PUBLICATIONS

Specialty Laboratories, Tests with Order Codes Beginning with Letters A–M; p. 1–11.
Specialty Laboratories, Tests with Order Codes Beginning with Letters N–Z; p. 1–10.
Saf–T–Pak STP–300 Insulated Packaging; pp. 1–4.
Cargopak, Packaging Products & Reference Materials; pp. 1–2.
Lexis Law Publishing's Code of Federal Regulations; Part 72—Interstate Shipment of Etiologic Agents [h1]; pp. 1–11.
Specialty Laboratories; #4952: Ritonavir MonitR test sheet.
Specialty Laboratories; #4951: Nelfinavir MonitR test sheet.
Federal Express Brochure; Rev 2/96.
National Jewish Medical and Research Center; *The Infectious Disease Pharmacokinetics Laboratory*; pp. 1–9, 1998.
National Jewish—Infectious Pharmacokinetics Laboratory (IDPL) Requisition, pp. 1–4.
http://www.pentose.com/Inactine.html.
http://www.liv.ac.uk/~hivgroup/labs/tdm.html.
Specialty Laboratories; #4967: Saquinavir MonitR™.
Jack Henion, et al; LC/MS Sample Preparation; Today's Chemist at Work, Feb. 1999.
Fred Klink; *New Sample Preparation Approaches to Biological Matrices for LC–MS*; Sample Prep Perspectives; vol. 17, No. 12 LCGC, pp. 1086–1093; Dec. 1999.
M J Ball; *Effect of two disinfectant treatments on laboratory analyses*; Journal of the Royal Society of Medicine, vol. 80, pp. 482–484; Aug. 1987.
2000 Test Catalog; Mayo Medical Laboratories; pp. 3–4, 97, 178; Dec. 31, 1999.
L.S. Matchette, et al.; *Glutaraldehyde Retain Its Disinfectant Properties in Presence of Hydroxypropylmethyl Cellulose (HPMC) Gel*; Journal of Biomedical Materials Research (Applied Biomaterials), vol. 33, pp. 101–105; 1996.
*Sterilization Filtration of Liquids*; Technical Report No. 26; PDA Journal of Pharmaceutical Science & Technology; Mar. 1998.
J. van Bueren, et al.; *Inactivation of human immunodeficiency virus type 1 by alcohols*; Journal of Hospital Infection (1994) 28, pp. 137–148.
Derwent Acc No 1990–135672 of JP 02083332A (1990). Deactivation of virus contained in protein preparations–comprises application of protein containing admixture of virus to ethanol.*
Derwent Acc No 2000–428972 of RU 2136747C1. Kostrovskii et al (1999). Method of inhibition of human immunodeficiency virus infection activity.*

* cited by examiner

METHOD FOR SIMPLIFIED SHIPPING OF CLINICAL SPECIMENS AND OPTIONAL DIRECT ANALYSIS

BACKGROUND OF THE INVENTION

1. Field of the Invention

The present invention relates to a method for the simplified shipping of clinical specimens, especially specimens that may contain an etiologic agent. The present invention further relates to the laboratory analysis of the shipped specimen, preferably directly upon receipt and without further substantial sample preparation.

2. Background of the Invention

The laboratory analysis of human or animal material, including, but not limited, to excreta, secreta, blood and its components, tissue, and tissue fluids is a necessity of modern medicine for the purposes of diagnosis. Most if not all Americans are familiar with "blood tests" used to determine their cholesterol level, the presence or absence of various microorganisms, and, depending upon level of sophistication, phenotyping, genotyping, etc. Such analysis is also used in therapeutic drug monitoring (TDM), which determines the quantity of a drug in the blood. TDM is now routine for approximately 20 different drugs for which dosing level is an issue and for which immnunochemical assays have been commercialized. TDM is extremely important for individualized therapy, and it is a tool used to avoid both toxic and sub-therapeutic blood concentrations (and the drug resistance that sub-therapeutic levels can induce in, for example, the treatment of infectious diseases).

One problem encountered in the laboratory analysis of clinical specimens is that oftentimes the laboratory where analysis is conducted is located apart from where samples are collected. Thus, the clinical specimen must somehow be transported to the site of the laboratory. The transportation of a clinical and, especially, an infectious specimen is highly regulated, complicated and expensive because of safety issues, health concerns, Department of Transportation regulations, and various other laws, rules, and regulations of the States and the United States, and foreign countries. In fact, the packaging and shipping standards for infectious substances in the United States are higher than those for any other class of dangerous goods except high-activity radioactive materials.

For example, Title 49 of the Code of Federal Regulations (CFR) governs the shipping of hazardous materials, and essentially encompasses the International Air Transport Association regulations regarding dangerous materials shipping, including the shipment of infectious substances that can affect a human. 49 CFR 171.8, 172.101, and 173.134, as well as 42 CFR, particularly sections 72.1–72.5, all incorporated herein by reference (current as of the filing date of this application), govern the shipment of etiologic agents (a viable microorganism or its toxin that causes, or may cause, human disease). As noted in 42 CFR 72.2, it is unlawful to knowingly transport or cause to be transported specimens and products that one reasonably believes may contain an etiologic agent unless certain packaging standards and requirements are met. Under 42 CFR 72.3, an extensive, non-comprehensive list of such etiologic agents is provided (incorporated herein by reference), and strict packing requirements, etc. are specified, as is a particular label that must be placed on the outer shipping containers of all materials containing etiologic agents. Of course, any package that possesses special labeling commands a significant surcharge that is payable to the shipping company. What is more, the special packaging that is required has become an industry in and of itself, and it is now common to spend at least $39 to purchase a box for a single sample (see, for example, part numbers STP100, STP300, and STP370, all found at www.cargopak.com/saftpak.htm and at www.saftpak.com). Even when a shipper does not reasonably believe that a clinical specimen contains an etiologic agent, readying such a sample for transport remains burdensome, expensive, and requires staffing by individuals who are fully apprised of all shipping regulations and who possess documentation of ongoing participation in training programs.

Another problem caused by the transport or shipping of clinical specimens to a laboratory for analysis is the integrity of the sample being shipped. If the sample is not maintained at a proper temperature during transport it is possible that the sample when analyzed is different from that when it was obtained, and that the results provided by the laboratory do not reflect the true state of the patient's condition. The incorporation of dry ice or cold packs in a package increases the weight and, hence the shipping cost. The convenience and timeliness of shipping temperature-controlled packages is low as well, since most receiving laboratories state that shipments should be made from Mondays to Thursdays only. What's more, because carbon dioxide is toxic, the transport of dry ice by aircraft adds significant regulatory burden.

The inventor knows of three organizations that openly promote the fee-for-service measurement of antiviral drug concentrations in body fluids of HIV-infected individuals. Specifically, these organizations are University of Liverpool, National Jewish Medical and Research Center, and Specialty Laboratories. In each case, the support literature from these organizations ask that untreated, known infectious plasma or serum be shipped, in a legally proper manner, to the analysis facility. Hence, the burden of precise compliance to all shipping regulations regarding etiologic agents, dry ice, etc. rests squarely on the shipper. Further, the real cost of sample analysis is inflated because of the packaging material costs, shipping surcharges, staffing by highly-trained shipping specialists, etc.

The practical result of the difficulties encountered in shipping a clinical specimen to a laboratory for analysis (i.e., shipping requirements, increased cost, maintenance of sample integrity, etc.) is illustrated by the website for Specialty Laboratories (www.specialtylabs.com), a research-based clinical reference laboratory that provides diagnostic, prognostic, and monitoring services. On this website under "Domestic & International Shipping Procedures" it is explained that the shipper of medical specimens is required to comply with the rules and guidelines for transport of such materials, and the shipper is ultimately responsible for all decisions that are made regarding packaging. Information is provided that outlines, with an intermediate level of detail, the various steps the shipper must go through in preparing a clinical specimen for shipment. Investigation into the shipment of such samples through overnight courier services, such as FedEx, has revealed that, beyond the normal fees based on weight and destination, substantially higher charges are incurred for samples labeled in accordance with the laws, rules and regulations that govern the shipping of clinical specimens that may contain etiologic agents.

OBJECTS OF THE INVENTION

It is one object of the invention to provide a method for the lawful shipment of clinical specimens that does not require compliance with U.S. laws, rules and regulations (including those of the States) regarding the shipment of samples or material that may contain an etiologic agent. (For applications in countries other than the U.S. the laws, rules and regulation are those of the examining country. All countries of the world are included such as Japan, the countries of Europe, South America, etc.)

It is a further object of the invention to provide a sample container useful for shipment of samples or material without the necessity of following the various laws, rules, and regulations regarding the shipment of etiologic materials.

It is a further object of the invention to provide method instructions and/or equipment to allow for the inactivation of clinical and etiologic specimens and their conversion from etiologic to non-etiologic or from biohazardous to non-biohazardous, the method equipment including a sample container for the shipment of the inactivated, non-etiologic sample in accordance with the invention method for shipment.

It is a further object of the invention to provide for the shipping of clinical specimens at ambient temperatures.

It is another object of the present invention to provide a process wherein biological, clinical, etc. samples that may be etiologic in nature are inactivated and made non-etiologic prior to shipping, lawfully shipped without compliance with at least one of the various laws, rules, and regulations regarding the shipping of etiologic materials, optionally received at an analysis laboratory, and optionally analyzed at said laboratory for example directly upon receipt and without further significant sample preparation.

These and other objects will become apparent as the invention is more thoroughly explained in the following detailed description.

DETAILED DESCRIPTION

In one embodiment the present invention relates to the shipment of a sample or material (hereinafter referred to as a clinical specimen) anywhere, including in interstate, intrastate, or international commerce. By "clinical specimen" the inventor means any human or animal material including, but not limited to, excreta, secreta, blood and its components, tissue, tissue fluids, and biological products that may or do contain an infectious or etiologic agent, excluding explanted medical devices and tissue, fluid, etc. adhering to an explanted medical device. A particularly preferred type of clinical specimen according to the invention is one that does contain an infectious or etiologic agent, where the term "etiologic agent" is defined herein as any microorganism or its toxin that causes, or may cause, human disease. The term "shipment" as used herein means physical transport to a directed location, whether effected by mail, courier, vehicle, ship, airplane, etc. and includes all common forms of shipment well known to those of ordinary skill in the art such as the national mail system, commercial courier services such as FedEx, Airborne, Emery Worldwide, DHL, etc., UPS, trucking services, car delivery services, bicycle couriers, pedestrian foot delivery services, etc. "Shipping" and "shipped" means the act of placing the thing to be physically transported in the hands of, the custody of, etc., a shipper such as the U.S. mail system, commercial courier services such as FedEx, Airborne, Emery Worldwide, DHL, etc., UPS, trucking services, car delivery services, bicycle couriers, pedestrian foot delivery services, etc. with delivery instructions and the subsequent shipment of the thing as received by the shipper. Excluded from the term "shipment" is the movement of the thing within a building or within a campus, or within a complex of associated buildings. Excluded from the term "shipping" is the act of placing the thing to be physically transported in the hands of, custody of, etc. a shipper with delivery instructions limited to delivery within a building or within a campus, or within a complex of associated buildings. In a preferred embodiment, the clinical specimen is shipped to (transported to) a testing laboratory for the purpose of being subjected to a test offered by the laboratory. For examples of tests useful herein, Specialty Laboratories, mentioned above, lists hundreds of such tests at www.specialtylabs.com under the heading of "test menu", all of which are hereby incorporated by reference. Examples include amikacin (test #4900), epinephrine (test #3270), phenobarbital (test #4142), zidovudine (test #4959), etc. Another listing of tests useful herein is the Mayo Medical Laboratories 2000 Test Catalog, 1999, Mayo Press, Rochester, Minn., incorporated herein by reference.

In a highly preferred embodiment, the clinical specimen is subjected to pre-shipping treatment that renders the clinical specimen non-infectious and non-etiologic (i.e., converts the clinical specimen to a "safe clinical sample") and that optionally also provides a sample that may be, and that preferably later is, capable of being directly subjected to the intended laboratory test without further significant sample pre-treatment.

Thus, a preferred embodiment of the present invention is a method for the shipping of clinical specimens lawfully without compliance with at least one of the various State, U.S., and, for countries other than the U.S., foreign national, as well as any applicable international, laws, rules, and regulations regarding shipment of materials that may contain etiologic agents, thereby avoiding the increased costs associated with shipping according to such laws, rules, and regulations and providing a safer, simpler, cost-effective method for the shipment of such samples. In a further preferred embodiment, the method includes receipt of the shipped clinical specimen (i.e., the safe clinical sample) by a laboratory, and in a highly preferred embodiment further includes the direct laboratory analysis of the sample as received (or after minimal preparation such as centrifigation, concentration, evaporation, and/or filtration). With the method of the present invention it is envisioned that the remote laboratory testing of a clinical specimen that has been converted into a safe clinical sample can be accomplished quickly (for example, within one day or less) and more cheaply than is the current state of the art with great efficiencies being realized in both the safer, simpler, easier, and cheaper method of shipping and, if laboratory testing is included in the method, with the cheaper and easier testing of the sample by either direct injection into the testing apparatus or direct subjection to the analysis method (or injection or subjection after minimal preparation such as centrifugation, concentration, evaporation, and /or filtration). It is envisioned that, with respect to TDM, the present method model will become a benchmark, allowing for relatively inexpensive, accurate, reproducible overnight turnaround for standard and even esoteric laboratory test results, thereby increasing the effectiveness of medical treatment and avoiding problems associated with sub-optimal therapy.

A preferred present invention method for converting a clinical specimen into a safe clinical sample, thereby converting the clinical specimen from a very expensive and somewhat complicated sample to ship into a very simple, safe, easy, cheap sample to ship, is treatment of the clinical specimen with enough water-miscible organic solvent to render the specimen non-etiologic and non-infectious (e.g., contact, mixing, etc.). Those of ordinary skill in this art know how to determine if a sample may contain an etiologic or infectious agent, and they know how to determine whether a sample has been rendered non-infectious and non-etiologic. In a highly preferred embodiment, alchohol (preferably reagent ethanol, pure ethanol, reagent alcohol, or denatured alcohol) is mixed with the specimen to provide preferably at least 70% by volume alcohol. As an example, in order to prepare a non-infectious, non-etiologic safe clinical sample for shipping according to the present invention, a particular volume (for example 1.00 ml) of a body fluid such as urine, plasma, cerebral spinal fluid, whole blood, serum, etc. is mixed with sufficient alcohol to provide a 70 vol. % alcohol solution. Of course, higher and lower amounts of alcohol can be utilized (such as 10, 20, 30, 40, 50, 60, 70, 80, 90, 95 and higher vol. %), but preferably 70 vol. % and above are used. In determining the amount of alcohol to add, one can assume that clinical specimens consisting of bodily fluids are essentially water. Thus, in the example above, 2.33 ml of anhydrous reagent alcohol would be added to the 1.00 ml of bodily fluid to provide at least a 70 vol. % alcohol solution. Of course, more or less alcohol could be added, if desired. In this way, method instructions and equipment may be provided that allows one to render a clinical specimen that may or does contain an etiologic and/or infectious agent non-infectious and non-etiologic and also, importantly, allow for lawful shipment of e.g., the safe clinical sample without compliance with at least one of the various laws, rules, and regulations regarding the shipment of specimens that may contain infectious or etiologic agents. If denatured alcohol is the solvent of choice, such a safe clinical sample may be subject to certain other rules and regulations regarding, for example, flammable samples, but the sample would not be subject to the significant and costly rules and regulations regarding shipment of, e.g., etiologic agents.

In addition to alcohol, other water-miscible organic solvents may be used for the invention purpose described above, including acetonitrile, methanol, and 2-propanol, among others. In a highly preferred embodiment, the solvent used does not affect the clinical specimen in a way that would affect the laboratory testing procedure intended for the specimen. It is particularly noteworthy that the invention method allows the user to avoid, if desired, the use of more hazardous and reactive chemicals that are often used for inactivation of etiologic agents, including chemicals such as formaldehyde, formalin, paraformaldehyde, glutaraldehyde, peroxygen-based compounds, and halogen-releasing compounds.

Another preferred present invention method for converting a clinical specimen into a safe clinical sample, thereby converting the clinical specimen from a very expensive and somewhat complicated sample to ship into a very simple, safe, easy, cheap sample to ship, is passage of the clinical specimen through a sterilizing filter to render the specimen non-etiologic and non-infectious. In a highly preferred embodiment, the clinical specimen is passed through a sterilizing filter that possesses pores preferably no greater than 0.2 microns in size. As an example, in order to prepare a non-infectious, non-etiologic safe clinical sample for shipping according to the present invention, a particular volume (for example 1.00 ml) of a body fluid such as urine, plasma, cerebral spinal fluid, whole blood, serum, etc. is passed through a 0.2 micron sterilizing filter. Of course, larger and smaller pore sizes can be utilized (such as 1.0 micron, 0.8 micron, 0.6 micron, 0.4 micron, 0.3 micron, 0.1 micron, 0.05 micron, 0.005 micron, and lower), but preferably 0.2 micron and smaller are used. In this way, method instructions and equipment may be provided that allows one to render a clinical specimen that may or does contain an etiologic and/or infectious agent non-infectious and non-etiologic and also, importantly, allow for lawful shipment of e.g., the safe clinical sample without regard to at least one of the various laws, rules, and regulations regarding the shipment of specimens that may contain infectious or etiologic agents.

Of course, the conversion methods noted above (filtration and solvent treatment) may be used in combination sequentially in any order or used together (e.g., the clinical specimen diluted with alcohol is passed through a filter).

Heat treatment of blood-derived samples at 56° C. can inactivate the HIV virus, for example. A heat treatment period ranging from 0.5 hours to as much as 5 hours (Resnick, et al., *JAMA* (1986) 255, 1887–91) is recommended, however, and even the shortest 0.5 hour exposure can modify free drug concentrations (Dasgupta, et al., *Ther. Drug Monit.* (1999) 21, 421–5). Such conditions are too harsh for labile molecules, as hydrolysis and other unwanted reactions will occur. Although heating of known infectious plasma, serum, etc. prior to or after mixing with water-miscible organic solvents and/or filter sterilization is labor intensive and unnecessary, the combination of these steps is included herein.

Also included herein, alone or in any combination with the conversion techniques described above, is the inactivation of the clinical specimen with any other agent or treatment prior to shipping. Such agents include INACTINE® products and those described in U.S. Pat. No. 5,891,705, incorporated herein by reference.

An important benefit of the present invention method for rendering a clinical specimen safe (i.e., non-infectious and non-etiologic), in addition to the lessened costs and requirements regarding lawful shipping, is that the sample, once rendered safe according to the present invention method (by solvent addition, filter sterilization, use of some other agent, heating, etc.), may be shipped without temperature control, meaning that traditional cooling with dry ice, etc. is not required when shipping the invention safe clinical sample. In this regard, dual savings are realized—the high cost and danger of shipping unsafe samples is avoided as is the high cost, regulatory burden, and difficulty of shipping samples that must be kept cold, for example with dry ice. Of course, temperature control may be used if desired, such as dry ice, ice packs, etc., and this is preferred for labile analytes.

In this sense, the present invention method of clinical specimen treatment (for example with a water-miscible organic solvent) so as to render the specimen safe followed by simple shipping lawfully without compliance with at least one of the various laws, rules and regulations regarding the shipment of, e.g., etiologic samples provides a new and useful method for shipping as well as a new and useful method that can capitalize on economies not previously recognized or utilized. In this way, the simple steps of adding, for example, alcohol to a clinical specimen, or filter sterilization, or a combination thereof, to render it safe followed by lawfully shipping the treated sample without regard to the laws, rules, and regulations that govern the shipment of, e.g., clinical specimens that may contain etiologic agents, provide a significant advance in the art not previously recognized. While it has previously been recognized that 70 vol. % denatured alcohol, heat, etc. can be used to inactivate etiologic agents and that filter sterilization can remove etiologic agents, it has not previously been recognized that if clinical specimens are so rendered prior to shipping they may then be shipped simply, lawfully, safely, cheaply, and easily without regard to the laws, rules, and regulations regarding shipment of etiologic specimens, and/or without regard to the maintenance of a certain temperature or general temperature control, such as cooling with dry ice, etc.

The "hardware" utilized in accomplishing what will be termed the "sample inactivation/shipping" aspect of the present invention described above is not particularly limited. Practical considerations preferably include containment of the sample in a closed, preferably non-leaking container that is not damaged or leached by the water-miscible solvent. With regard to packaging for shipping, practical considerations should be borne in mind in view of the realities encountered by the various commercial and governmental shipping concerns. While no special accommodations are required, it is preferred that shipping occur in an envelope, box, etc. that will survive intact its transport to the ultimate destination.

Several sample collection containers and assemblies are known in the art, and all may be used herein. Examples include GB1,542,411, U.S. Pat. No. 1,594,370, 3,163,160, 3,915,806, 4,336,880, 4,311,792, 4,604,360, 4,732,850, 4,788,985, 4,813,432, 5,313,959, 5,266,266, 5,425,915, 5,658,531, 5,710,041, 5,726,062, 5,786,227, 5,786,228, 5,859,374, 5,879,635, 4,211,323, 4,150,950 and 5,511,558, all incorporated herein by reference. One particularly preferred embodiment for use in the sample inactivation/shipping embodiment of the present invention is a container that itself contains an inner container. The inner container holds the water-miscible solvent of the invention, for example, reagent alcohol. The volume of solvent held in the inner container (e.g., a frangible ampoule) may be pre-measured in accordance with the amount of clinical specimen that is directed to be placed in the container. In using this arrangement the clinical specimen is placed in the container, the container is optionally closed, and the inner container is manipulated such that the water-miscible organic solvent mixes with, contacts, etc. the clinical specimen such that it is rendered non-infectious and non-etiologic. If desired, this solution could then be passed through a sterilizing filter assembly. As noted above, it is preferred that the final volume percent of water-miscible organic solvent is at least 70%, including 75, 80, 85, 90 and greater than 90% by volume, and that the filter pores are less than 0.2 micron, including 0.1 micron, 0.05 micron, and 0.005 micron. Ethanol contents that are 70–75% by volume show excellent performance in HIV-inactivation assessments (van Bueren et al., *J. Hosp. Infection* (1994) 28, 137–148; Druce et al., *J. Hosp. Infection* (1995) 30, 167–180; both incorporated herein by reference). Filters with pore sizes of 0.2 micron and smaller are used to sterilize medicines, fluids, and blood-derived products that are meant for intravenous, intramuscular, etc. use (Brown et al., *Dev. Biol. Stand.*, "Viral Safety and Evaluation of Viral Clearance from Biopharmaceutical Products." (1996) 88, 319–326; McKinnon et al., *Am. J. Hosp. Pharm.* (1993) 50, 1921–1936; Anonymous, PDA *J. Pharm. Sci. Technol.*, "Parenteral Drug Association Technical Report No. 26, Sterilizing Filtration of Liquids." (1998) 52 (No. 3, Supplement), 1–31; all incorporated herein by reference). It is preferred that the container can be sealed such that it need only be placed in a high-quality plastic bag containing absorbent prior to placement in an envelope, box, etc. to be shipped and thus configured such that it can withstand such shipping without breakage, leakage, etc. Thus, and in accordance with the present invention, method equipment may include one or any combination of a clinical specimen container, a shipping container, method instructions, etc. The shipping container may be pre-addressed and is preferably configured such that the specimen container may be shipped therein. Optionally present in the method equipment, optionally located in the specimen container, is a certain volume of water-miscible organic solvent or instructions regarding the use of water-miscible organic solvents optionally with method equipment components. Also optionally present in the method equipment, optionally attached to the specimen container, is a sterilizing filter assembly and/or instructions regarding the use of a sterilizing filter assembly with other, e.g., method equipment components. The water-miscible organic solvent is preferably provided such that it can be contacted with the clinical specimen, sealed within the specimen container, and the specimen container shipped in the shipping container, for example to a testing laboratory, lawfully without regard to the various laws, rules, and regulations regarding the shipment of, e.g., etiologic agents and optionally without temperature controls such as packing on dry ice, etc. In a preferred embodiment, the water-miscible organic solvent itself, or the method equipment (or, if the method equipment does not contain solvent, the instructions regarding the solvent) may contain an internal standard (or instructions concerning the use of an internal standard) that allows a testing laboratory to quantitatively determine the amount of whatever is being tested for in the specimen.

Another embodiment of the present invention relates to the analysis of safe clinical samples, made safe (e.g., converted) according to the invention. In this further embodiment, a safe clinical sample is simply directly analyzed with minimal or no sample pre-treatment. For example, a clinical specimen that has been diluted to 70 vol. % reagent alcohol may be directly analyzed on an LC system or an LC-MS system, or analyzed after centrifugation, concentration, evaporation, and/or filtering. The system of analysis could not be more simple: the safe clinical sample containing, e.g., 70 % by volume reagent alcohol, is simply directly (or after centrifugation, concentration, evaporation, and/or filtering) injected into a laboratory instrument for analysis or subjected to the desired laboratory test. If one wishes to preserve the performance of the instrument, protective measures known in the art such as a in-line filter, a guard column, or a column-switching valve, etc. may be taken. Lab tests that do not depend upon specimen-associated enzyme activity and whose target (analyte) being tested for does not precipitate due to water-miscible organic solvent treatment, are preferred. Lab tests whose target (analyte) being tested for does pass through a sterilizing filter assembly are preferred. If an internal standard is not added to the clinical specimen at the point of origin or point of shipping, it may be added at the recipient laboratory prior to analysis. While it is known that some laboratories use water-miscible organic solvents, concentrated acids, and metal salts to precipitate proteins from samples prior to analysis, it is believed that 1) acetonitrile is used in the vast majority of cases and that 2) these methods have been used on an in-house basis only, and not on clinical specimens prior to shipping.

In a highly preferred embodiment, a further method is provided that combines the sample inactivation/shipping embodiment described above in combination with the direct analysis of the sample upon receipt at a laboratory. This model provides for highly effective and cost efficient shipping due to the non-etiologic and non-infectious nature of the sample and the lack of a requirement for temperature control (dry ice, etc.) while at the same time providing a sample that is "analysis ready," meaning that no further sample preparation is required prior to laboratory testing. In this way, a method is described that provides extremely simple and quick turnaround of laboratory test results for clinical specimens.

EXAMPLE

The following example contemplates obtaining (receiving) a clinical specimen at a location remote from the testing laboratory, converted into a safe clinical sample according to s the invention, and shipping to the laboratory preferably without compliance with at least one law, rule or regulation concerning the shipment of a material that may contain an etiologic or infectious agent.

After a package is received from the courier, etc., the sample is entered into the laboratory information management system by way of barcode scanning, etc. The accuracy of the inactivation (conversion) step, wherein the clinical specimen was, e.g., previously added to the method equipment, can be assessed by weighing the safe clinical sample, by determining the ethanol:water ratio present in the sample, etc. The sample is then either centrifuged, concentrated, evaporated, filtered, or not given any further treatment. The sample may then be injected (100 μL, CTC Analytics, for example) directly into an HPLC system (Shimadzu, for example), then analytes and internal standard may be eluted from the column (a 4.6 mm Keystone Betasil column, for example) using a gradient or a isocratic mobile phase system (water, acetonitrile, formic acid, for example). The analytes and internal standard may be detected and quantitated by a mass spectrometer (PE Sciex triple-quadrupole, for example). The batch may then be approved by a medical technologist or a physician, then each report is signed and transmitted to the requesting physician.

Examples of preferred embodiments described herein, which those of ordinary skill in the art are now capable of understanding, making and using in view of the present specification, include the following:

A. A method of shipping, comprising contacting a clinical specimen with sufficient water-miscible organic solvent to convert the clinical specimen into a safe clinical sample, and shipping said safe clinical sample.

B. A method of shipping, comprising passing a clinical specimen through a sterilizing filter assembly with sufficiently small pores to convert the clinical specimen into a safe clinical sample, and shipping said safe clinical sample.

C. A method of shipping, comprising contacting a clinical specimen with sufficient water-miscible organic solvent and passing through a sterilizing filter assembly with sufficiently small pores to convert the clinical specimen into a safe clinical sample, and shipping said safe clinical sample.

D. The method of A, B, and C, wherein said safe clinical sample is shipped to a testing laboratory.

E. The method of A, B, C, and D, wherein said safe clinical sample is lawfully packaged and labeled for shipping in a manner that does not comply with at least one State or Federal law, rule, or regulation regarding the shipping of material which may contain an infectious or etiologic agent. The regulations include Titles 42 and 49 of the code of Federal Regulations, both incorporated herein by reference, and the IATA regulations, also incorporated herein by reference.

F. The method of A, B, C, D, and E, wherein said safe clinical sample is packaged without any provision of sample temperature control or maintenance.

G. The method of A, B, C, D, E, and F, wherein said safe clinical sample is received by said laboratory and directly subjected to laboratory analysis without substantial sample preparation.

H. The method of A, B, C, D, E, F, and G, wherein the laboratory analysis determines the amount or concentration of a chemical in the sample.

I. The method of A, B, C, D, E, F, G, and H, wherein the laboratory analysis determines the amount or concentration of a drug in the sample.

J. The method of A, B, C, D, E, F, G, H, and I, wherein said water-miscible organic solvent is ethanol.

K. The method of A, B, C, D, E, F, G, H, and I, wherein said water-miscible organic solvent is denatured alcohol.

L. The method of A, B, C, D, E, F, G, H, and I, wherein said sterilizing filter assembly possesses pores of 0.2 microns or less.

M. The method of A, B, C, D, E, F, G, H, I, J, K and L, wherein said clinical specimen does contain an etiologic agent.

N. Equipment for effecting any method noted above.

O. The equipment of N, further containing invention method instructions.

P. The equipment of N and O, containing a shipping container that, when shipped, does not comply with at least one law, rule or regulation concerning the shipping of infectious or etiologic agents.

With regard to this invention being utilized in foreign countries, and in any PCT or foreign application based upon this application, it is to be understood that the various laws, rules, and regulations referenced above include those laws, rules and regulations of all foreign countries, territories, possessions, etc. and each foreign country, possession, territory, etc.

Obviously, numerous modifications and variations of the present invention are possible in light of the above teachings. It is therefore to be understood that within the scope of the appended claims, the invention may be practiced otherwise than as specifically described herein.

What is claimed is:

1. A method of shipping, comprising converting a clinical specimen into a safe clinical sample, and shipping said safe clinical sample, wherein said safe clinical sample is non-infectious and non-etiologic.

2. The method of claim 1, wherein said clinical specimen is converted into safe clinical sample by passing said clinical specimen through a filter.

3. The method of claim 1, wherein said clinical specimen is converted into a safe clinical sample by passing said clinical specimen through a filter having pores no greater than 0.2 microns in size.

4. The method of claim 1, wherein said clinical specimen does contain an etiologic agent.

5. The method of claim 1, wherein said clinical specimen is converted into said safe clinical sample by a process comprising contacting said clinical specimen with a water-miscible organic solvent and:passing said mixture of solvent and specimen through a filter.

6. The method of claim 5, wherein said filter has pores no greater than 0.2 microns in size.

7. The method of claim 5, wherein said water-miscible organic solvent comprises ethanol or denatured alcohol.

8. The method of claim 1, wherein said safe clinical sample is shipped without any provision for sample temperature control or maintenance.

9. The method of claim 1, wherein said clinical specimen is converted into said safe clinical sample by a process comprising contacting said clinical specimen with a water-miscible organic solvent.

10. The method of claim 9, wherein said water-miscible organic solvent comprises ethanol or denatured alcohol.

11. The method of claim 1, wherein said safe clinical sample is shipped to a testing laboratory.

12. The method of claim 11, wherein said clinical specimen does contain an etiologic agent.

13. The method of claim 11, wherein said safe clinical sample is shipped without any provision for sample temperature control or maintenance.

14. The method of claim 13, wherein said safe clinical sample is received by said laboratory and directly subjected to laboratory analysis without substantial sample preparation.

15. The method of claim 14, wherein the laboratory analysis determines the amount or concentration of a drug in the sample.

16. The method of claim 14, wherein the laboratory analysis determines the amount or concentration of a chemical in the sample.

17. The method of claim 11, wherein said safe clinical sample is received by said laboratory and directly subjected to laboratory analysis without substantial sample preparation.

18. The method of claim 17, wherein the laboratory analysis determines the amount or concentration of a drug in the sample.

19. The method of claim 17, wherein the laboratory analysis determines the amount or concentration of a chemical in the sample.

20. The method of claim 17, wherein said clinical specimen does contain an etiologic agent.

* * * * *